(12) United States Patent
Golan

(10) Patent No.: US 6,610,029 B1
(45) Date of Patent: Aug. 26, 2003

(54) NEEDLE-LESS INJECTING DEVICE

(75) Inventor: Ygal Golan, Amberg (DE)

(73) Assignee: Deutscher Zahnarzt Verlag (DZV), Amberg (DE)

(*) Notice: Subject to any disclaimer, the term of this patent is extended or adjusted under 35 U.S.C. 154(b) by 0 days.

(21) Appl. No.: 09/534,788

(22) Filed: Mar. 24, 2000

(30) Foreign Application Priority Data

Mar. 24, 1999 (DE) .......................... 199 13 344

(51) Int. Cl.⁷ .................. A61M 5/20; A61M 5/30; A61M 5/315
(52) U.S. Cl. ................. 604/135; 604/68; 604/220
(58) Field of Search ................. 604/68, 71, 72, 604/131, 134, 135, 181, 186, 207–211, 220, 224

(56) References Cited

U.S. PATENT DOCUMENTS

| | | | |
|---|---|---|---|
| 4,103,684 A | * 8/1978 | Ismach | 604/71 |
| 4,623,332 A | 11/1986 | Lindmayer et al. | |
| 4,722,728 A | 2/1988 | Dixon | |
| 5,026,343 A | * 6/1991 | Holzer | 604/68 |
| 5,049,125 A | 9/1991 | Accaries et al. | |
| 5,062,830 A | * 11/1991 | Dunlap | 604/68 |
| 5,318,522 A | * 6/1994 | D'Antonio | 604/135 |
| 5,879,327 A | * 3/1999 | DeFarges et al. | 604/68 |
| 6,083,197 A | * 7/2000 | Umbaugh | 604/68 |

FOREIGN PATENT DOCUMENTS

| | | |
|---|---|---|
| DE | 33 28 173 A1 | 2/1985 |
| EP | 0 276 158 A2 | 7/1988 |
| EP | 0 286 798 A2 | 10/1988 |
| EP | 0 294 272 B1 | 12/1988 |
| EP | 0 370 571 A2 | 5/1990 |
| EP | 0 406 778 A1 | 1/1991 |
| FR | 2 689 018 A1 | 10/1993 |
| FR | 2689 018 A1 | 10/1993 |
| WO | WO 94/07554 | 4/1994 |
| WO | WO 95/03844 | 2/1995 |
| WO | WO 95/16481 | 6/1995 |
| WO | WO 95/27523 | 10/1995 |
| WO | WO 96/24398 | 8/1996 |
| WO | WO 96/36381 | 11/1996 |
| WO | WO 97/13536 | 4/1997 |

* cited by examiner

*Primary Examiner*—Michael J Hayes
(74) *Attorney, Agent, or Firm*—Mueting, Raasch & Gebhardt, P.A.

(57) ABSTRACT

The present invention is an improved needle-less injector device for the injection of fluids into the patients body. The injector device consists of a chassis, a nozzle on one end, a section for carpules containing the fluids to be injected, a piston, a spring-element acting on the piston, a compressing-mechanism for the spring-element and a release-mechanism. The compressing-mechanism can be connected to a coupling device of a standard dental driving unit.

4 Claims, 1 Drawing Sheet

NEEDLE-LESS INJECTING DEVICE

Figure 1:
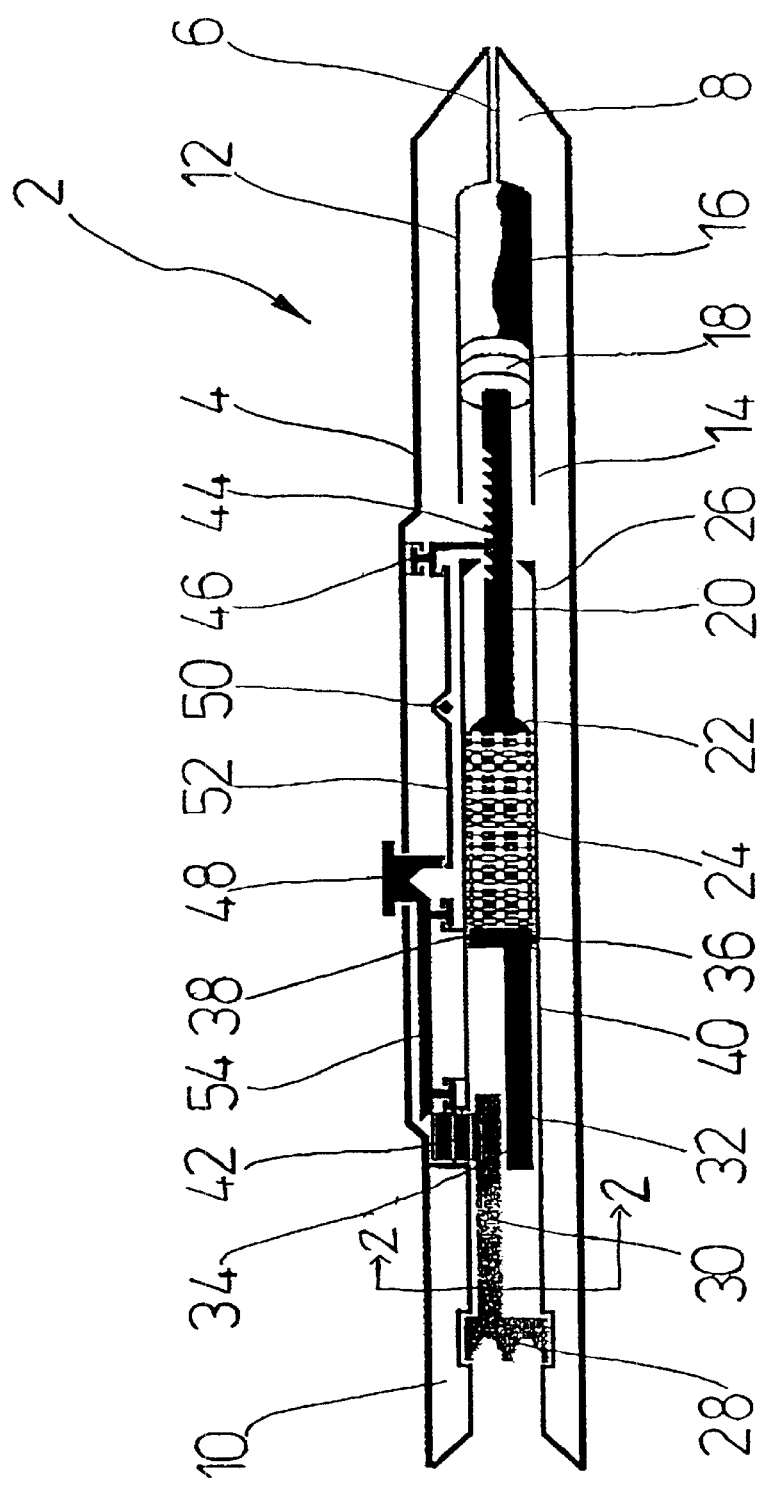

The present invention is a needle-less injection device for the injection of liquids into the body of a patient, particularly in the oral region.

At present, the most common way of delivering local anesthetics is with the use of needles. Unfortunately, for many patients, the most unpleasant moment of a dental visit is the needle prick. Furthermore, the use of needles carries the risk of needlestick injuries and cross-contamination. We have therefore aimed to design an injection device that does not require needles. Although several needle-less devices are currently available, many of them have several disadvantages. They are rather large and heavy due to their complicated loading mechanisms. A frequently used product on the market has a weight of about 590 g, is 28 cm long and costs approximately US$1700. In addition, the large devices pose psychological disadvantages for the patient.

The present invention aims to make an improved injection device available. With the features of our claim, this aim has been achieved.

WO-A-96/36381 describes a injection device for high pressure injection of fluids or particle-containing fluids. This injection device has a piston in a pressure chamber that opens into an injection orifice. The fluid-driving force is produced by an elastic stroke on the piston that accelerates to the stop on the opposing side. The volume of the pressure chamber is bigger than the extruded fluid volume.

Other needle-less injection devices include those described by WO-A-94/07554, WO-A-95/03844, WO-A-96/24398, WO-A-95/27523; WO-A-95/16481, WO-A-97/13536, EP-A-370 571, EP-A-286 798, EP-A-27,6 158 or DE-A-33 28 173.

The invention is based on the idea that the needle-less injection device has a coupling on the opposite side of the nozzle, similar to those found in conventional dental devices such as drive drills, burr polishers etc. This device can be activated by connection to the coupling of any usual dental unit. A rotating-element that is meshed to a gearwheel and another axial movable rotating-element is provided on the opposite side of the nozzle . These rotating-elements produce tension in the spring-element.

The needle-less injecting device 2 has the advantages of having no complicated loading mechanisms to produce tension in the spring-element, and that the device itself can be built comparably small and simple. It is made of few parts, requires little or no maintenance, and can be sterilized easily. Customary carpules containing anesthetics can also be used. Compared to needle injection devices, there is no danger of needle fracture and the risk of allergy or toxic reactions can be minimallsed through the reduction of the quantity of administered anesthetics. Another advantage of the needle-less technique is that the patient does not have to be afraid of pain, During the injection the patient only feels a short tap. Thereby, the acceptance for this method of injection will rise, and better treatment success can be expected.

The needle-less device is described in the following figures:

FIG. 1: Schematic longitudinal section through the needle-less injection device.

Figure 2:
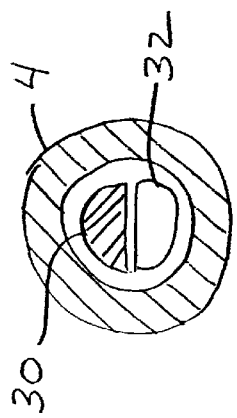

FIG. 2: Schematic of the half-round profiles of the rotation elements.

The injection device described in FIGS. 1 2 shows a cylindric chassis 4 with one end 8 containing a nozzle 6 and the opposite end containing a coupling device 10. The chassis could be made out of metal or a metallic alloy, but can also be fabricated from plastic, glass or other easily sterilizable materials.

The nozzle connects to a section in the chassis 14 designed to host standard carpules 12 containing the injection fluid 16. For high-pressure injection, there is an axially movable piston 18 in the chassis 4 that is able to move inside the sealed carpule 12. If the piston 18 is moved rapidly inside the carpule 12 in the direction of the nozzle 6, the fluid will be injected under high pressure out of the needle-less injecting device 2. The depth of fluid penetration will vary according to the pressure in the patient's tissue, On the opposite side of the nozzle 6 of the piston, a piston-bar 20 that is connected through a springdisk 22 with the spring-element 24 could be installed. The piston-bar 20 is for the needle-less injecting device 2 is optional, since the spring-element 24 could also act directly on the opposite side of the nozzle 6 located side of piston 18. The spring-element could be a pressure-spring (e.g., a spiral pressure spring or springdisk-package) a gas pressure-spring, a hydraulic spring-element or a space-containing compressible material.

The spring-element is preferably axially movable, and embedded in a guiding installation 26 of the chassis 4. The needle-less injecting device shown in FIGS. 1 2 is shown with a compressed spring-element 24. A compressing device is used to compress the spring-element 24. This device can be connected to the coupling of a conventional dental unit intended to drive drills, polishers etc. Therefore, on the end 10 of the chassis 4 a coupling-element 28 to is intended to be connected to the (not shown) driving unit. This coupling-element is one part of the first, essentially axial fixated rotating-element. This rotating-element shows an extended part 30 in the axial direction, with a preferably half-round transverse sectioned profile. The loading mechanism shows a second axial movable rotation-element 32 that can also be rotated by the coupling-element 28. The second rotation-element 32 also shows an preferably half-round transverse sectioned profile. Together, both elements form 34 a cylindric outer circumference. Thereby a turn of rotation-element 30 turns the second rotation-element 32. The second rotation-element 32 shows an axial leading section 36 supporting the spring-element 24. On the axial leading section 36 there is preferably an external thread 38 that slides in the internal thread 40 of the guiding installation. Activation of the dental unit driving mechanism leads to rotation of the rotation-elements 30 and 32, wherein the second rotation-element is displaced according to the gradient of thread 38 or 40, which leads to a reduction of the interleaving region 34 with increasing bias.

To obtain a defined bias, the needle-less injection device would preferably have a limiting device to limit the axial movement of the second rotation-element 32. This limiting device could be made of a stopping-device for the second rotation-element and a slide-coupling on the driving device or the coupling-element 28. When the axial leading section 36 stops on the stopping-device, the axial mobility of the second rotation-element 32 is blocked, so that the first rotation-element 30 with the coupling-element 28 can no longer turn. With the help of the slide-coupling, the rotation-movement will no longer be transferred to the compressing device. Alternatively the limiting-device can be made out of a gearwheel 42 meshed to the rotation-elements 30 and 32. The gearwheel is built in such a way as to predictably limit the axial position of the second rotation-element and additional rotation of both rotation-elements. Different fluid quantities will be ejected according to individual anesthesia techniques. This could be obtained through a calibrated formation of the gear-tooth system of rotation-element 32. Furthermore, in this version a slide-device in the driving unit or in the region of the coupling-element (not shown) is advantageous.

To trigger the needle-less injecting device 2, the piston 18 has to be unlocked, so the fluid in the carpule 12 can be ejected through the nozzle 6 under high pressure. Therefore, there could be a snap-device 44 on the piston bar 20 or on the piston 18, that connects with an snap-element 46 on the chassis 4. The snap-device 44 could be made out of a longitudinal tooth system on the piston 18 or the piston bar 20, that snaps inside the snap-element 46. In order to trigger the needle-less injecting device 2 the snap-element 46 has to disengage from the snap-device 44. Therefore, there is a release button 48 on the chassis 4, that will, if pressed, release the piston 18 through a lever arm 52 that turns around a turning point 50. The spring-element 24 releases und pushes the piston 18 through the piston-bar 20 into the carpule 12 and fires the contained liquid 16 with high pressure out of the nozzle 6.

Furthermore, there can be an installation 54, connected to the releasing button 48 to stop the limiting device. The installation 54 could be integrated into the trigging button 48, so the limiting device can be discharged.

The needle-less injecting device 2 can be uncoupled during injection of fluid to allow for easy handling. The needle-less injecting device 2 can also be used with the coupled driving unit.

What is claimed is:

1. A needle-less injecting device for injecting fluids into the body of a patient, the device comprising:

an injection nozzle located at one end of a chassis;

an injection fluid section within the chassis that is in fluid communication with the injection nozzle;

a piston movable along an axial direction within the injection fluid section, wherein movement of the piston towards the injection nozzle forces injection fluid within the injection fluid section to move through the injection nozzle;

a spring element located within the chassis, the spring element comprising a bias condition and a release position, whereby the spring element moves the piston towards the injection nozzle that when released from the bias condition to the release condition;

a compressing device located within the chassis, wherein the compressing device comprises a first rotating element and a second rotating element, wherein the first rotating element and the second rotating element overlap along the axial direction within the chassis, wherein the first rotating element and the second rotating element each comprises a half round profile where the first rotating element and the second rotating element overlap along the axial direction within the chassis, wherein the first rotating element and the second rotating element are coupled such that rotation of the first rotating element rotates the second rotating element, wherein the second rotating element moves along the axial direction when the first rotating element is rotated, and further wherein rotation of the compressing device moves the spring element from the release condition to the bias condition; and a rotatable coupling element operably connected to the compressing device, the coupling element capable of coupling with a conventional rotating dental device.

2. A device according to claim 1, wherein the coupling element and the injection nozzle are located at opposite ends of the chassis along the axial direction.

3. A device according to claim 1, wherein the first rotating element is connected to the coupling element.

4. A device according to claim 1, further comprising a release mechanism operably connected to the piston such that the release mechanism retains the spring element in the bias condition until the piston is released, whereby the spring element moves to the release condition.

* * * * *